United States Patent
Phillips et al.

(10) Patent No.: US 7,480,042 B1
(45) Date of Patent: Jan. 20, 2009

(54) LUMINESCENCE REFERENCE STANDARDS

(75) Inventors: J. Michael Phillips, San Carlos, CA (US); Aldrich N. K. Lau, Palo Alto, CA (US); Mark F. Oldham, Los Gatos, CA (US); Kevin S. Bodner, Belmont, CA (US); Steven J. Boege, San Mateo, CA (US); Donald R. Sandell, San Jose, CA (US); David H. Tracy, Norwalk, CT (US)

(73) Assignee: Applied Biosystems Inc., Foster City, CA (US)

( * ) Notice: Subject to any disclaimer, the term of this patent is extended or adjusted under 35 U.S.C. 154(b) by 170 days.

(21) Appl. No.: 11/173,609

(22) Filed: Jun. 30, 2005

Related U.S. Application Data

(60) Provisional application No. 60/584,890, filed on Jun. 30, 2004.

(51) Int. Cl.
*G01J 1/10* (2006.01)
(52) U.S. Cl. .................................... 356/243.1
(58) Field of Classification Search ... 356/243.1–243.8; 436/8
See application file for complete search history.

(56) References Cited

U.S. PATENT DOCUMENTS

| | | | |
|---|---|---|---|
| 5,838,435 A * | 11/1998 | Sandison | ................. 356/243.1 |
| 6,002,482 A | 12/1999 | Rothfritz et al. | |
| 6,191,851 B1 | 2/2001 | Kirkham et al. | |
| 6,242,114 B1 | 6/2001 | Yamasaki et al. | |
| 6,259,524 B1 | 7/2001 | Hofstraat et al. | |
| 6,348,965 B1 | 2/2002 | Palladino et al. | |
| 6,352,672 B1 | 3/2002 | Mabile et al. | |
| 6,428,752 B1 | 8/2002 | Montagu | |
| 6,646,737 B2 | 11/2003 | Tortonese et al. | |
| 6,948,843 B2 * | 9/2005 | Laugharn et al. | ............. 366/127 |
| 2002/0047884 A1 | 4/2002 | Nagashima et al. | |
| 2002/0048817 A1 | 4/2002 | Yekta et al. | |
| 2002/0164817 A1 | 11/2002 | Neriishi | |
| 2003/0012702 A1 | 1/2003 | Hudson | |
| 2003/0030797 A1 | 2/2003 | Palladino et al. | |
| 2003/0086085 A1 | 5/2003 | Harju et al. | |
| 2003/0174321 A1 | 9/2003 | Samsoondar et al. | |
| 2004/0008343 A1 | 1/2004 | Pawluczyk et al. | |
| 2004/0036868 A1 | 2/2004 | Jones et al. | |
| 2004/0259260 A1 * | 12/2004 | Gunstream et al. | ............. 436/8 |

* cited by examiner

*Primary Examiner*—Gregory J Toatley, Jr.
*Assistant Examiner*—Juan D Valentin

(57) ABSTRACT

Systems, and components thereof, for detecting and/or analyzing light. These systems can include, among others, optical reference standards for calibrating, validating, and/or monitoring light-detection systems, before, during, and/or after sample analysis.

18 Claims, 6 Drawing Sheets

LUMINESCENCE REFERENCE STANDARDS

CROSS-REFERENCE TO RELATED APPLICATIONS

This application claims a priority benefit under 35 U.S.C. § 119(e) from U.S. Patent Application No. 60/584,890 filed Jun. 30, 2004, which is incorporated herein by reference.

INTRODUCTION

The identity, properties, and interactions of samples such as biomolecules can be analyzed by detecting light emitted by or otherwise originating from the sample. The emitted light can arise naturally in the sample and/or be induced by illumination or other stimulus. In either case, the emitted light can be detected, and the illumination optionally can be provided, by a suitable light-detection system. The ability of the light-detection system to collect and quantify emitted light and thus to characterize samples is determined in part by the extent to which the light-detection system is and can be calibrated.

SUMMARY

The present teachings provide systems, and components thereof, for detecting and/or analyzing light. These systems can include, among others, optical reference standards for calibrating, validating, and/or monitoring light-detection systems, before, during, and/or after sample analysis.

DESCRIPTION OF VARIOUS EMBODIMENTS

The present teachings provide systems, including components thereof and aids thereto, for detecting and/or analyzing light. These systems can include, among others, optical reference standards for calibrating, validating, and/or monitoring light-detection systems, including components and/or aspects thereof, before, during, and/or after sample analysis. Suitable uses can include aligning portions of a light detection system, relative to one another and/or one or more samples. Suitable uses also can include validating system performance, including attainment and/or maintenance of threshold conditions. Suitable uses also can include monitoring and/or correcting for underages, overages, and/or variations in illumination intensity, among others. These underages, overages, and/or variations can occur with respect to space and/or time, and can be determined and/or corrected for before, during, and/or after sample analysis. Thus, the optical reference standards can be used in methods of calibrating, validating, and/or monitoring a light-detection system and/or methods of performing an assay (e.g., involving measuring properties of the reference standard and sample, and performing a correlation and/or correction based on such measurements), among others.

Exemplary usages of the optical reference standards can include (1) aligning optical components, (2) validating system performance, (3) confirming performance and settings for excitation and/or emission filters (before or after their installation in the same or a different instrument), (4) verifying threshold illumination (e.g., intensity and/or uniformity) and detection (e.g., sensitivity) parameters, (5) compensating for spatial and/or temporal variations in illumination, (6) tracking drift in illumination intensity and/or looking for signs of (and acting to prevent) impending component (e.g., light source) failure, (7) locating and/or aligning sample holders, or portions thereof (e.g., in high-density array grids), and/or (8) calibrating intensity, wavelength, and/or other parameters (e.g., by comparing values measured in a sample against known values measured from the standard), among others. Additional usages and applications are described below, particularly in Section III and Example 4, among others.

Exemplary users can include manufacturers, service and maintenance personnel, and/or end users, among others.

Figure 1:
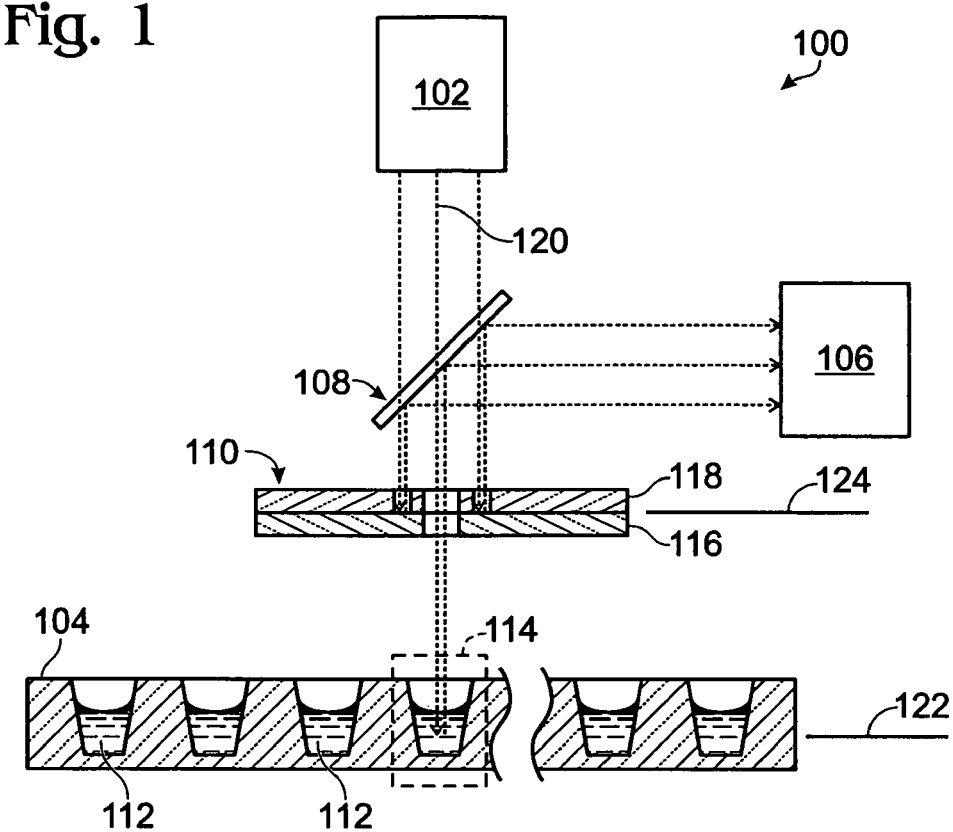
FIG. 1 is a schematic view of an exemplary light-detection system, showing selected optical components and an optical reference standard, in accordance with aspects of the present teachings.

FIG. 1 shows an exemplary light-detection system 100, including selected optical components 102-108 and an optical reference standard 110, in accordance with aspects of the present teachings.

The light-detection system generally comprises any mechanism for detecting (and optionally analyzing) light from a sample. Suitable systems can include (1) a light source 102 for producing light for illuminating, and/or inducing a suitable or desired response from, a sample, (2) a sample-support device 104 for supporting one or more samples 112 at an examination area 114, (3) a detector 106 for detecting light transmitted or otherwise originating from a sample and optionally converting the detected light into a representative signal, and/or (4) an optical relay structure 108 for directing light between the light source and examination area, and the examination area and detector, among others. These and other aspects of the light-detection system are described below; see particularly Section II and Example 3. Exemplary light-detection systems, including components and uses thereof, also are described in the following patent application, which is incorporated herein by reference: U.S. Provisional Patent Application Ser. No. 60/584,525, filed Jun. 30, 2004, titled Distributed Light Detector of inventors Charles S. Vann and Steven Boege.

The optical reference standard generally comprises any mechanism for monitoring and/or calibrating a light-detection system, including components and/or aspects thereof. The reference standard can include a light-producing (e.g., luminescent) portion 116 and/or a light-blocking (e.g., mask) portion 118, among others. The reference standard can be disposed in the light-detection system, transiently or permanently, at any suitable position(s). Typical positions lie in or along the optical path 120, such as in the object plane 122 (i.e., the plane, typically at least partially coextensive with the examination area, that is occupied by the sample and imaged by the detector during sample analysis) and/or in an intermediate position 124 (e.g., an intermediate image plane) operatively disposed along the incident illumination path between the light source and object plane, among others. The reference standard can be positioned manually and/or automatically, as desired. The reference standard can be placed into and/or taken out of the light path in connection with each use and/or related series of uses, and/or the reference standard can be positioned permanently in the light path. The reference standard (or a suitable set of reference standards) can be housed within the detection system, where it can be moved more easily into or out of position or, alternatively, maintained in a fixed position. These and other aspects of the optical reference standard are described below; see particularly Section I and Examples 1 and 2.

The following sections describe further aspects of the present teachings, including (I) reference standards, (II) light-detection systems, (III) applications, and (IV) examples, among others.

I. OPTICAL REFERENCE STANDARDS

The optical reference standard, as noted above, generally comprises any mechanism for monitoring and/or calibrating a light-detection system, including components and/or aspects thereof.

Figure 2:
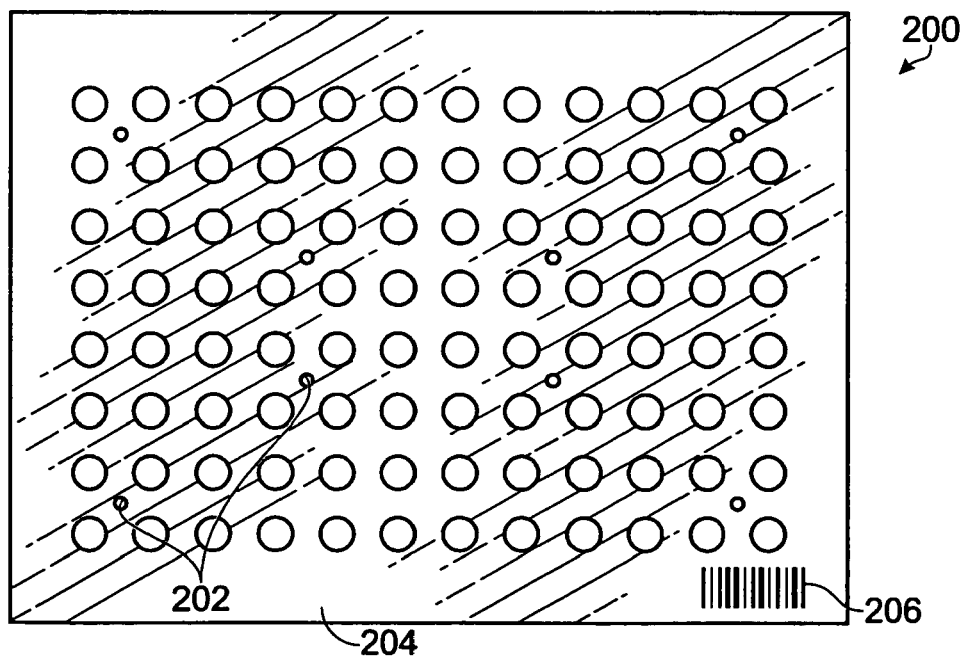
FIG. 2 is a top view of an exemplary optical reference standard, in accordance with aspects of the present teachings.

FIG. 2 shows an exemplary optical reference standard 200, in accordance with aspects of the present teachings. This reference standard can include a light-producing (e.g., luminescent) element 202, for producing light, and/or a light-blocking (e.g., mask) element 204, for selectively blocking light, among others. These elements can be present and/or employed singly and/or in combination. Thus, in a given light-detection system, and/or for a given application, a light-producing element can be used, a light-blocking element can be used, and/or both a light-producing and a light-blocking element can be used. Moreover, if used together, the light-producing and light-blocking elements can be at least substantially separate or at least substantially unitary, depending on embodiment. Thus, in some cases (e.g., FIG. 3), the light-blocking element can be supported by or ancillary to the light-producing element, whereas, in other cases (e.g., FIG. 4), the light-producing element can be supported by or ancillary to the light-blocking element. In both cases, the light-producing and light-blocking elements simply can be placed in contact or proximity, or the light-producing and light-blocking elements can be joined and/or rendered at least partially coextensive using any suitable mechanism (including adhesives, fasteners, fusion, and/or so on).

The light-producing and light-blocking elements (as well as other components of the reference standard) can have any suitable shape or size. Commonly, these elements, or portions thereof, will be at least substantially planar. Such planar portions can be configured so that, in use, the plane is at least substantially perpendicular to the optical axis of the light-detection system. More generally, the reference standard (or components thereof) can be shaped and/or sized to match a standard sample holder, or portion thereof, such as a microplate, a biochip, and so on.

The properties of the optical reference standard can be correlated with properties of the intended sample(s). The correlation can include matching properties of the light produced by the standard with properties of the light produced by the sample(s), including wavelength, intensity, polarization, and/or the like. The correlation also can include matching the concentration, size, and/or position of luminophore(s) in the reference standard and sample(s).

The reference standard can include one or more ancillary elements, helpful to function, but not involved directly in light production. These ancillary elements can include an identification element 206, among others. The identification element can include any mechanism or feature for identifying the reference standard and/or a characteristic or use thereof. Suitable mechanisms or features can include a barcode and/or a shape, pattern, marking, aperture, or the like associated with the reference standard. Suitable information can include a unique identifier (e.g., a serial number), general properties of the reference standard (e.g., emission wavelength profile, the identities of luminophores suitable for use with the standard, assay conditions or identifiers, operator information, date, etc.), and/or so on. The information provided by the identification element can be used for any suitable purpose, including setting detection-system parameters (e.g., filter settings), inputting data to be stored electronically with the assay results, and/or so on.

The reference standard can be configured for use in any desired optical configuration, including trans (excitation light directed to and emission light collected from opposite sides of the sample), epi (excitation light directed to and emission light collected from same side of the sample), and oblique (excitation light directed and emission light detected at oblique angles), among others. For example, for trans illumination, associated support components typically would be transparent to at least one of the excitation and emission light, whereas for epi illumination such supports can be transparent or opaque.

The reference standard can be placed in and/or removed from desired positions in the light-detection system by any suitable mechanism. For example, the reference standard can be placed in the examination area by hand, and/or carried to and/or from the examination area (or other position) by an automated conveyor mechanism, among others. The conveyor mechanism can be the same as or different than any mechanism (such as a stage) used to convey sample holders to and/or from the examination area. Where the same conveyor is used for both standards and samples, the conveyor can be adapted to hold standards and samples simultaneously and/or sequentially. Where different conveyors are used for standards and samples, the two conveyors can be configured and controlled independently and/or coordinately. In either case, the standard optionally can be configured (e.g., shaped and/or sized) like the sample holder, simplifying handling, and helping to ensure that the standard successfully emulates the sample, sample conditions, and/or aspects thereof.

These and other aspects of optical reference standards are described below, including (A) relationships between light-producing and light-blocking elements, (B) light-producing elements, and (C) light-blocking elements, among others. Attributes of these elements, and components thereof, can be mixed and matched as appropriate or desired.

I.A Relationships Between Light-Producing and Light-Blocking Elements

Figure 3:
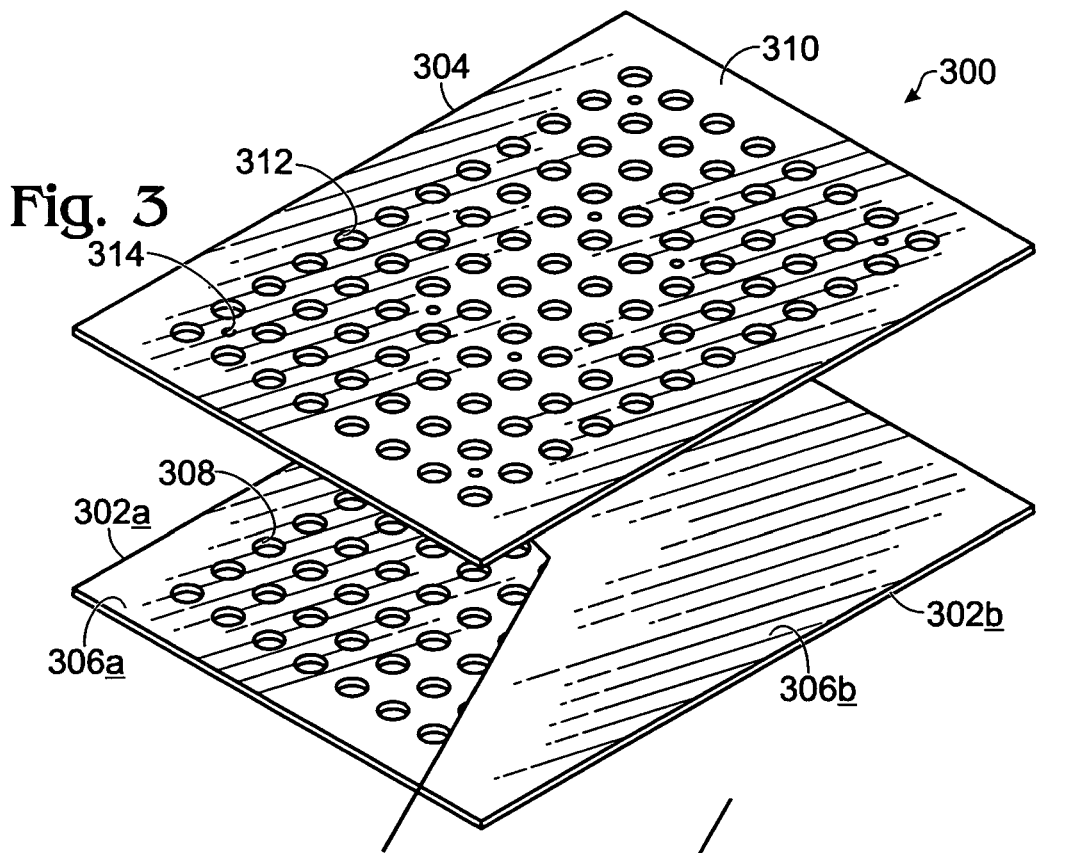
FIG. 3 is an exploded isometric view of two exemplary embodiments of an optical reference standard, with an upper light-blocking portion and a lower light-producing portion, in accordance with aspects of the present teachings. The embodiment shown at left is configured generally for use in an optical plane intermediate between a light source and the object plane. The embodiment shown at right is configured generally for use in the object plane.
Figure 4:
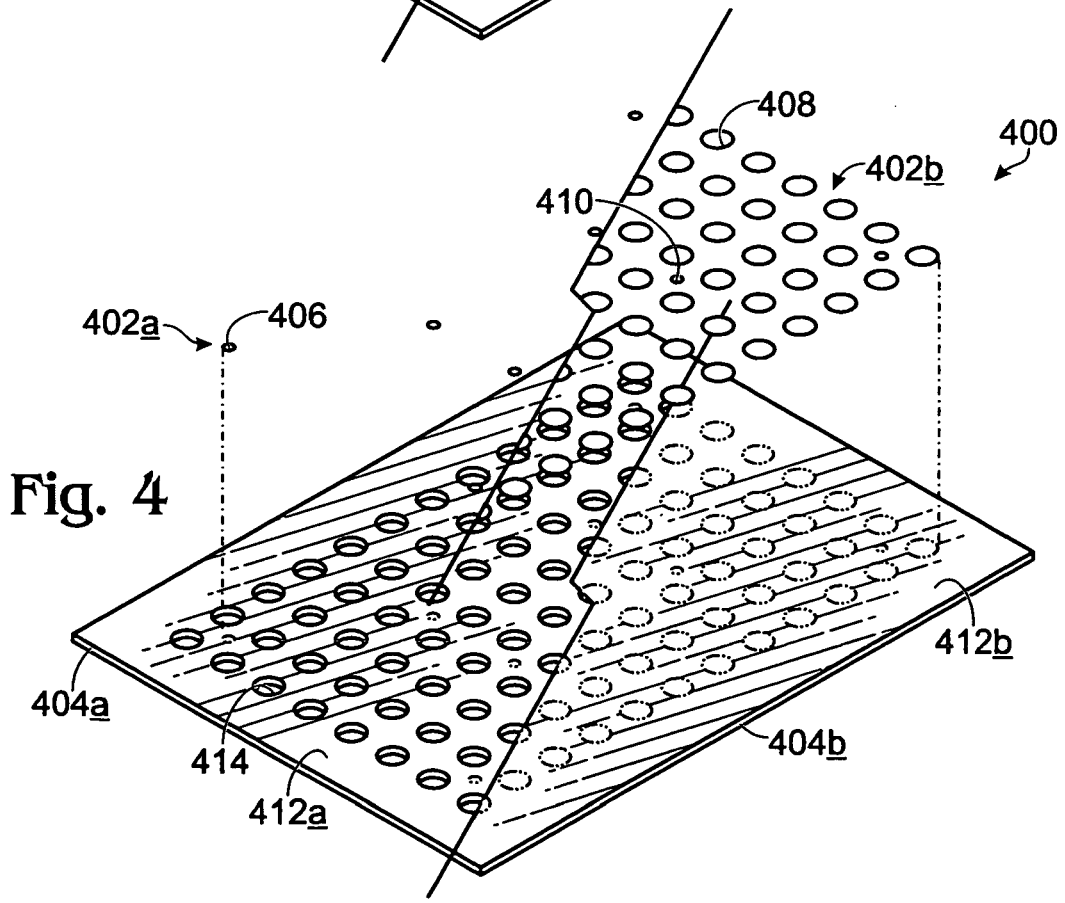
FIG. 4 is an exploded isometric view of two alternative exemplary embodiments of an optical reference standard, with an upper light-producing portion and a lower light-blocking portion, in accordance with aspects of the present teachings. The embodiment shown at left is configured generally for use in an optical plane intermediate between a light source and the object plane. The embodiment shown at right is configured generally for use in the object plane.

This section describes exemplary relationship between the light-producing and light-blocking elements, in the context of several examples; see FIGS. 3 and 4.

I.A(i) Exemplary Relationships 1

FIG. 3 shows two exemplary embodiments of a first optical reference standard 300, with a first set of relationships between light-producing and light-blocking elements, in accordance with aspects of the present teachings. These reference standards are particularly suitable for use in epi illumination.

Reference standard 300 can include a light-producing element 302a,b (corresponding to embodiments "a" and "b") and a light-blocking element 304, among others. Light-producing element 302a in embodiment "a" can include a luminescent portion 306a and a set of transparent portions 308. Light-producing portion 302b in embodiment "b" can include a luminescent portion 306b but does not (necessarily) include any transparent portions. Light-blocking element 304 (in both embodiments) can include an opaque portion 310 and first and second sets 312, 314 of transparent portions, respectively. The first set of transparent portions is configured for sample excitation; specifically, in the pictured embodiment, there are 96 apertures configured to allow light to travel to and from 96 samples in a 96-well microplate. The second set of transparent portions is configured for calibration; specifically, in the pictured embodiment, there are 8 inter-well apertures configured to allow light to travel to and from an associated light-producing element. Here, transparent portions can transmit at least a substantial portion of incident light, and opaque portions can block at least substantially all incident light.

Embodiment "a" (i.e., the left side of the reference standard (302a+304)) is configured for placement in an intermediate optical plane, between the light source and sample, facilitating use before, during, and/or after sample analysis. In use, the first set of transparent portions (312) in the light-blocking element can be aligned with the transparent portions (308) in the light-producing element, allowing excitation light, at first preselected positions, to impinge on samples and induce production of emission light that passes back through the aligned sets of transparent portions and onto the detector, where it can be used for sample analysis. Moreover, the second set of transparent portions (314) in the light-blocking element can be aligned with emissive portions (306a) of the light-producing element, allowing excitation light, at second preselected positions, to impinge on an adjacent light-producing element and induce production of emission light that passes back through the first set of transparent portions and onto the detector, where it can be used for calibration. These concepts are further illustrated in FIG. 1.

Embodiment "b" (i.e., the right side of the reference standard (302b+304)) is configured for placement in an object plane, facilitating use before and/or after sample analysis. Here, in use, both the first (312) and second (314) sets of transparent portions in the light-blocking portion can be aligned with emissive portions (306b) of the light-producing element, allowing excitation light to impinge on and induce production of emission light from both regions, where it can be used for calibration.

I.A(i) Exemplary Relationships 2

FIG. 4 shows two exemplary embodiments of a second optical reference standard 400, with a second set of relationships between light-producing and light-blocking elements, in accordance with aspects of the invention. These reference standards, like those in FIG. 3, are particularly suitable for use in epi illumination.

Reference standard 400 can include a light-producing element 402a,b (corresponding to embodiments "a" and "b") and a light-blocking element 404a,b, among others. Light-producing element 402a in embodiment "a" can include a set of light-emissive portions 406, and light-producing element 402b in embodiment "b" can include first and second sets 408, 410 of light-emissive portions. Light-blocking element 404a can include an opaque portion 412a and a set 414 of transparent portions. Light-blocking element 404b can include an opaque portion 412b but does not (necessarily) include any transparent portions. The pictured embodiment is configured for use with a 96-well microplate, in parallel with FIG. 3, although, like in FIG. 3, the general principles can be applied in any suitable manner. Here, the light-emissive portions (406, 408, and 410) are supported by (i.e., contact, rest upon, and/or are partially or completely embedded in) the light-blocking element (404a or 404b, respectively). The light-producing portions (in this and/or other embodiments) can independently have the same and/or different spectral outputs (i.e., can independently produce light with the same and/or different color(s)).

Embodiment "a" (i.e., the left side of the reference standard (402a+404a)) is configured for placement in an intermediate optical plane, between the light source and sample. In use, light can travel to and from the sample through transparent portions 414, for use in sample analysis, and light emission can be induced from light-emissive portions 406, for use in calibration. This embodiment most closely resembles embodiment "a" in FIG. 3.

Embodiment "b" (i.e., the right side of the reference standard (402b+404b)) is configured for placement in an object plane. Here, in use, light emission can be induced from both the first (408) and second (410) sets of light-emissive portions, for use in calibration. This embodiment most closely resembles embodiment "b" in FIG. 3.

I.B Light-Producing Elements

The light-producing element generally comprises any mechanism for producing (and/or redirecting) light as part of an optical reference standard for monitoring and/or calibrating a light-detection system. This element can be distinguished by the nature and/or arrangement of the mechanism(s) used to produce the light and/or the disposition of the mechanism(s) relative to an associated light-blocking element and/or a light-detection system, among others. Thus, in some embodiments, and unless otherwise noted, the light-producing element can be configured to produce light by any suitable mechanism, including emission, reflection, transmission, refraction, diffraction, and/or scattering, among others. Here, emission can include luminescence, including photoluminescence (e.g., fluorescence, phosphorescence, etc.) and/or chemiluminescence, among others. Conversely, in other embodiments, the light-producing element can be configured to produce light only via particular mechanisms, for example, via luminescence mechanisms, as described below for subtraction-based and addition-based reference standards. In either case, the light produced by the light-producing element can be used "as is" and/or filtered to alter its wavelength, intensity, polarization, and/or coherence, among others.

The optical reference standard can be configured to produce light primarily or exclusively at preselected wavelengths and/or over preselected ranges of wavelengths. Toward this end, in some "subtraction-based" embodiments, the light produced by the reference standard can be obtained by "subtracting" undesired spectral components from a relatively broadband emission; see Section I.D below. In other "addition-based" embodiments, the light produced by the reference standard can be obtained by "adding" desired spectral components from two or more materials; see Section I.E below. In yet other embodiments, the light produced by the reference standard can be obtained by a combination of these and/or other mechanisms.

Luminescence-based light-producing elements can be based on photoluminescence, in which the light-producing element is induced to emit emission light by illumination with suitable excitation light. The emission light corresponding to excitation with particular excitation light can be characterized by an emission spectrum, and the excitation light corresponding to particular emission light can be characterized by an excitation spectrum, as described below. Typically, the excitation light will lie at least primarily to one side of some cutoff wavelength, and the emission light will lie at least primarily to the other side of the cutoff wavelength. For example, with single-photon excitation, the wavelength(s) of the excitation light typically would be shorter than some cutoff wavelength (corresponding to relatively higher energies), and the wavelength(s) of the emission light typically would be longer than the cutoff wavelength (corresponding to relatively lower energies). Conversely, with multi-photon excitation, these wavelength differences typically would be reversed. The differences between the wavelengths of the excitation and emission light can facilitate the separation and distinguishable detection of emission light.

I.C Light-Blocking Elements

The light-blocking element generally comprises any mechanism for blocking (and/or redirecting) light as part of an optical reference standard for monitoring and/or calibrating a light-detection system. This element can be distinguished by the nature and/or arrangement of the mechanism(s) used to block the light and/or the disposition of the mechanism(s) relative to an associated light-producing element and/or a light-detection system, among others. The light-blocking (or optically opaque) element can be configured to block light by any suitable mechanism, including absorption and/or reflection, refraction, diffraction, and/or scattering out of the optical path, among others. The blocked light can represent any amount between at least about half and at least about all (or entirely all) of the incident light, among others.

The light-blocking element can be formed of any suitable material, including but not limited to plastic and/or metal such as aluminum or steel (e.g., sheet metal) having a non-fluorescing coating or paint, such as black anodizing.

The light-blocking element can include both light-blocking (opaque) portions, as described above, and light-transmitting (transparent) portions that allow passage of excitation and/or emission light, as appropriate or desired. The opacity and transparency of these portions can be absolute or relative. Collectively, the opaque and transparent portions can create a mask or pattern that allows selective illumination of the light-producing portion of the reference standard and/or samples in a light-detection system, for example, as described above for FIGS. 1, 3, and 4.

The transparent portions (and thus the opaque portions) can have any suitable shape and size. For example, the transparent portions can be sized and spaced to correspond to and/or allow selective illumination of a light-producing element and/or sample holder, among others. Thus, in specific embodiments, the reference standard can include 96, 384, or 1536 transparent portions, among others, corresponding to wells in a 96, 384, or 1536-well microplate, among others. Alternatively, or in addition, the reference standard might include another number of transparent portions corresponding to inter-well calibration marks.

The transparent portions can have any form capable of transmitting excitation and/or emission light, or portions thereof. Thus, the transparent portions can include apertures and/or optically transparent (or partially transparent) materials (at least in the wavelength range(s) of interest). The optically transparent materials can include glass, quartz, plastic and/or the like, among others.

I.D Subtraction-Based Reference Standards

Subtraction-based reference standards generally comprise any reference standards, or portions thereof, in which output light with the desired spectral components is obtained by producing light with both desired and undesired spectral components and then "subtracting" the light with the undesired spectral components. The subtraction-based reference standards can include, among others, (1) a relatively broadband emissive element, and (2) a relatively narrowband subtractive element. The emissive element generally is capable of outputting light (e.g., emitting luminescence) over a greater number or range of wavelengths than ultimately desired as output light from the reference standard (i.e., outputting light with both "desired" and "undesired" spectral components). The subtractive element generally is configured to reduce or eliminate the undesired spectral components, thereby increasing the relative proportion of desired spectral components.

Figure 5:
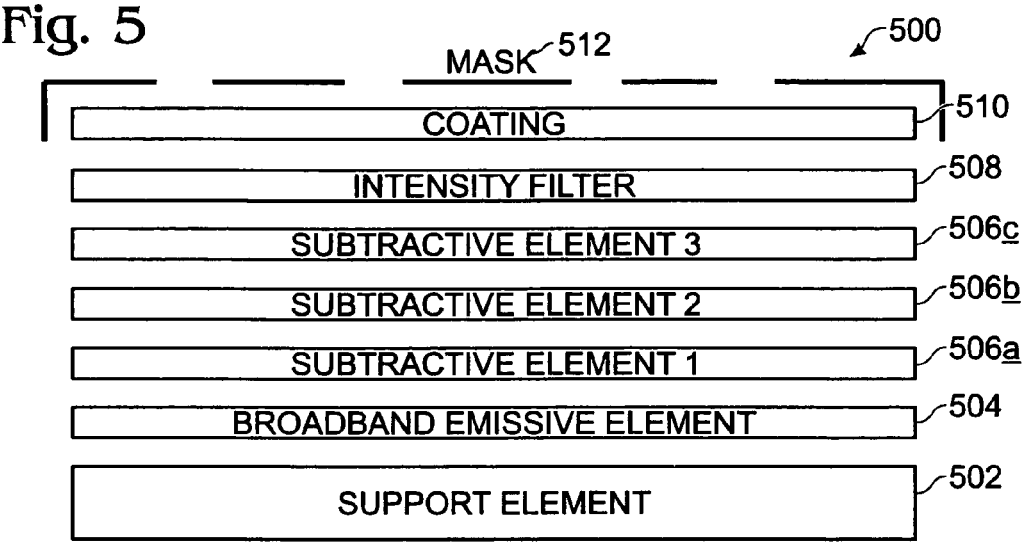
FIG. 5 is a schematic sectional view of an exemplary subtraction-based optical reference standard, showing light-producing and light-blocking elements, in accordance with aspects of the present teachings.

FIG. 5 shows an exemplary subtraction-based reference standard 500. This exemplary standard can include a support element 502, a relatively broadband emissive element 504, a relatively narrowband subtractive element 506, an intensity filter element 508, a protective coating 510, and/or a mask (light-blocking element) 512, among others. These elements can be discrete (e.g., separate, defined layers) and/or interdigitated (e.g., interwoven and/or blended layers (with shared or overlapping functions)). Typically, the subtractive and filter elements will be disposed so that they will lie in use between the emissive element and the detector, and the coating element will be disposed near an outer surface of the reference standard. More generally, these and other elements of the subtraction-based (or other type of) reference standard can be arranged in any suitable order.

Support element 502 generally comprises any material, or property thereof, configured to provide structural support for the reference standard. Exemplary support materials include glass and/or plastic, among others. The support element can take any suitable form, with any suitable dimensions, such as a planar slab (e.g., sized like a microscope slide, a gel, and/or a microplate, among others) and/or a standard sample holder (e.g., configured and sized like a microplate, a biochip, or the like).

Emissive element 504 generally comprises any mechanism for generating or producing light over a greater number or range of wavelengths than the number or range(s) output by the reference standard (i.e., with desired and undesired spectral components). The emissive element can produce such light by any suitable mechanism, including transmission, reflection, absorption (generally selective absorption and/or absorption and re-emission), and/or emission, among others. Transmission generally includes passing light through the element, unaltered, or altered via absorption, refraction, diffraction, scattering, and/or the like. Emission generally includes any mechanism for producing light within the emissive element, including photoluminescence and/or chemiluminescence, among others. Photoluminescent sources produce photoluminescence light in response to illumination with suitable excitation light. Photoluminescence can include fluorescence (i.e., light produced by a singlet-to-singlet electronic transition) and/or phosphorescence (i.e., light produced by a triplet-to-single electronic transition), among others. Chemiluminescent sources produce chemiluminescence light associated with a chemical reaction (e.g., as part of a reaction that produces an intermediary or product in an excited electronic state that subsequently decays by production of light) and/or electrical stimulation (e.g., electrochemiluminescence). Chemiluminescence can include bioluminescence (i.e., light produced by a biological reaction), among others. Suitable emissive elements can include luminophores, fluorophores, dyes, pigments, and/or the like. These elements can be wet or dry, liquid or solid, dissolved or suspended, homogeneous or heterogeneous, and so on.

Subtractive element 506 generally comprises any mechanism for altering the spectrum of the excitation and/or emission light, or portions thereof. The spectral filter element generally acts to reduce or eliminate emission at selected wavelengths and/or over selected ranges of wavelengths (i.e., to reduce or remove undesired spectral components). These functions can be accomplished via any suitable mechanism, using a single subtractive element or a combination of subtractive elements. Suitable subtractive elements include filter elements such as (1) short-pass (cut-off) filters, which pass short-wavelength light and reject long-wavelength light, (2) long-pass (cut-on) filters, which pass long-wavelength light and reject short-wavelength light, (3) bandpass filters, which pass light with a particular wavelength (or range of wavelengths) and reject light with lower and higher wavelengths, and/or (4) band reject (or notch) filters, which reject light with a particular wavelength (or range of wavelengths) and pass light with lower and higher wavelengths, among others. Short-pass and long-pass filters (also know as edge filters) can be characterized by a cut-on or cut-off wavelength, among others, and bandpass and band reject filters can be characterized by a center wavelength and a bandwidth, among others. Suitable subtractive elements can include thin-film (e.g., metallic and/or interference) coatings, colored filter glass, holographic filters, liquid-crystal tunable filters, and/or acousto-optical tunable filters, among others. These subtractive elements can work by absorbing, reflecting, and/or bending (refracting or diffracting) light, among others. In some embodiments, the subtractive element can work by filtering portions of the excitation light whose absorption gives rise to undesired spectral components of the emission.

Intensity filter element 508 generally comprises any mechanism for altering the intensity of the excitation and/or emission light, or portions thereof. In some cases, the intensity filter element can reduce the overall intensity of the excitation light and/or emission light, substantially independent of wavelength. For example, the filter could reduce overall excitation intensity to reduce photobleaching of the standard, and it could reduce overall emission intensity to better match corresponding sample intensities, among others. In other cases, the intensity filter element can reduce the intensity of the excitation and/or emission light, according to wavelength. For example, the filter could adjust the relative intensities of different spectral components of the emission light (e.g., making the height of multiple emission peaks more (or less) similar by using a filter element that blocks selectively a portion of the brighter (or dimmer) peaks). In any case, the strength of the intensity filter can be substantially uniform with position, so that intensities from all portions of the reference standard are reduced proportionally, or the strength of the intensity filter can vary with position, so that intensities from some portions of the reference standard are reduced more than the intensities from others (e.g., to create a pattern). Suitable intensity filter elements include neutral density filters, among others.

Protective coating 510 generally comprises any mechanism for protecting the reference standard from unnecessary or unwanted exposure to environmental conditions. These conditions can include high humidity, harsh or corrosive chemicals, rough handling, and so on. Thus, the protective coating can be relatively impervious to water and/or other commonly encountered chemicals, and/or resistant to scratching, bending, and/or breaking, among others. Consistent with these functions, the coating can be disposed about an outward or exterior surface of the reference standard, particularly on portions of the standard likely to encounter the unwanted condition(s). Suitable coating materials include plastics, among others, particularly plastics that are at least partially transparent to excitation and/or emission light employed during use of the reference standard.

Mask 512 generally comprises any mechanism for selectively rejecting most or all of the emission from selected portions of the reference standard. Suitable masks were discussed above; see particularly Section I.C. The mask can be positioned to block excitation light and/or emission light, depending in part on the embodiment and intended application.

Specific exemplary subtraction-based reference standards are described below, in Example 1.

I.E Addition-Based Reference Standards

Addition-based reference standards generally comprise any reference standards, or portions thereof, in which output light with the desired spectral components is obtained by "adding" together or combining light from different components that individually produce light having only a subset of the desired characteristics. Light from addition-based reference standards can be used "as is" or spectrally filtered (as with the subtraction-based reference standards) to remove any undesired components present after the addition. Such filtering can be accomplished, among other ways, using a spectral filter that is integral to or otherwise associated with the standard and/or part of a light-detection system. Addition-based standards optionally can include one or more of the various components described above for subtraction-based standards, including a support, a filter element, a coating, and/or a mask, among others. Luminescent (and other) components of the addition-based reference standard can take any suitable form, including wet or dry, continuous or discrete, separate or blended, planar or formed, planar or sample-holder shaped, and/or so on. In some embodiments, the luminescent components can be selected and/or adapted such that they can be excited using light with one wavelength (or range of wavelengths), while emitting at two or more distinguishable wavelengths (or ranges of wavelengths). Exemplary addition-based reference standards can include photoluminescent nanocrystals (e.g., "quantum dots"), luminescent glass, and so on. Specific exemplary addition-based reference standards are described below, in Example 2.

II. LIGHT DETECTION SYSTEMS

The light-detection system, as noted above, generally comprises any mechanism for detecting (and optionally analyzing) light from a sample. This system can include (1) a light source for producing light for illuminating, and/or inducing a suitable or desired response from, a sample, (2) a sample-support device for supporting one or more samples at an examination area, (3) a detector for detecting light transmitted or otherwise originating from a sample and optionally converting the detected light into a representative signal, and/or (4) an optical relay structure for directing and/or processing light between the light source and examination area, and/or between the examination area and the detector, among others.

The components of the light-detection system can be selected and/or configured according to the intended application, desired level of automation, and so on. Typically, the light source produces light that is directed by the optical relay structure along an incident optical path so that it impinges on or illuminates one or more samples disposed at one or more locations in the examination area. (This portion of the light-detection system can be omitted or simply left unused in chemiluminescence applications.) Output light emitted, transmitted, reflected, scattered, and/or otherwise originating from the sample(s) then is directed by the optical relay structure along an output optical path onto the detector. The light-detection system can include an optional controller adapted to control one or more system components, including, among others, the light source(s), the detector(s), and/or a registration device configured to bring one or more samples and the examination area into registration for analysis of the sample(s). The controller can be configured to control or otherwise coordinate the illumination of samples and/or the detection of outputted radiation with the relative position(s) of sample(s) and examination area. The light-detection system also can include additional components, such as (1) a fluidics mechanism to add, remove, and/or mix sample components, (2) a sample-handling mechanism to convey samples and/or sample holders to and/or from the examination area and/or registration device, (3) an analysis mechanism to analyze or interpret assay results, and/or (4) a sample-identification mechanism such as a barcode reader to identify samples and/or sample holders, and optionally to configure or operate system components accordingly, among others.

These and other aspects of light-detection systems provided by the present teachings are described below, including (A) light sources, (B) optical relay structures, (C) sample-support devices, (D) registration devices, (E) color separators, (F) detectors, (G) miscellaneous optical elements, and (H) controllers, among others, as well as relationships and interactions there between.

II.A. Light Sources

The light source (102) generally comprises any mechanism for producing light capable of illuminating, and/or inducing a suitable or desired response from, a sample. For example, when used in an optical assay, light from the light source can, as a result of illuminating a sample, produce emitted (e.g., photoluminescence) light, transmitted light, reflected light, and/or scattered light, among others. These different forms of light can be present exclusively, or in various combinations, and can include ultraviolet, visible, and/or infrared light, among others. The light source optionally can induce a similar or related response from a suitably positioned optical reference standard.

Exemplary light sources can include continuous wave and pulsed lasers, arc (e.g., xenon) lamps, incandescent (e.g., tungsten halogen) lamps, fluorescent lamps, electroluminescent devices, laser diodes, and/or light-emitting diodes (LEDs), among others. Such light sources can be capable of use in one or more illumination modes, including continuous and/or time-varying (e.g., pulsed or sinusoidally varying) modes, among others, depending on system configuration and/or intended application. For example, an arc lamp or continuous wave laser can be used to provide continuous illumination, and a pulsed laser can be used to provide intermittent illumination. Such light sources also can produce coherent, incoherent, monochromatic, polychromatic, polarized, and/or unpolarized light, among others. For example, an arc lamp can be used to provide (at least initially) incoherent, polychromatic, unpolarized light, and a laser can be used to provide (at least initially) coherent, monochromatic, polarized light, among other possibilities.

The light source can be used alone but would be used more commonly in combination with various optics and/or other mechanisms (such as the optical relay structures described below). These optics and/or other mechanisms can be used to alter the nature of the light output by the light source (e.g., its color (spectrum or chromaticity), intensity, polarization, and/or coherence, among others). Alternatively, or in addition, these optics and/or other mechanisms can be used to direct and/or alter the size, shape, and/or numerosity of the light beam(s) (e.g., to illuminate selected locations in an examination area with one or more light beams). The light that ultimately is incident on the sample(s) can be produced by one or more light sources, and can be directed and/or modified by one or more optical devices operatively disposed between the light source(s) and the examination area. The resultant light beam or beams can be one or more of various forms, including but not limited to diverging, collimated, and converging, among others. This beam or beams can be directed onto an examination area in a manner inducing light production from one or more samples located in a plurality of locations within the examination area.

II.B. Optical Relay Structures

The optical relay structure (108) generally comprises any mechanism(s) for directing, transmitting, and/or conducting light between two points, such as from a light source toward a sample (or examination site) and/or from a sample (or examination site) toward a detector. These structures can stand alone and/or be portions of or integral to other system components, such as the light source, color separator, and/or detector, among others. The optical relay structures can be configured to direct one or more light beams, in the same or different directions, along the same, multiple, or different optical paths.

The optical relay structures can include any suitable combination of optical elements. These elements independently can be part of a single (e.g., excitation or emission) relay structure, or can be shared between two or more relay structures. Exemplary optical elements can include (1) reflective elements, such as concave, planar, and/or convex mirrors, among others, (2) refractive elements, such as converging, diverging, concave, convex, and/or planoconvex lenses, including circular and/or cylindrical lenses, among others, and/or (3) transmissive or conductive elements, such as glass or quartz fiber optics and/or liquid light guides, among others.

The optical relay structure(s) can be selected, in conjunction with the light source(s) and/or detector(s), to allow any suitable or desired combinations of illumination and/or detection. For example, these components can be arranged to allow same-side, (locally) anti-parallel or straight-on ("epi") illumination and detection, such as top illumination and top detection, or bottom illumination and bottom detection, respectively. Alternatively, or in addition, these components can be arranged to allow opposite side, (locally) parallel or straight-through ("trans") illumination and detection, such as top illumination and bottom detection, or bottom illumination and top detection, respectively. Alternatively, or in addition, these components can be arranged to allow illumination and/or detection at oblique angles. For example, illumination light can impinge on the bottom of a sample holder at an acute angle (e.g., about 45 degrees) relative to detection. Such oblique illumination and detection can reduce the amount of excitation light reaching the detector, relative to straight-on epi systems (light source and detector directed at about 90 degrees to sample holder) or straight-through trans systems (light source directed through a sample holder directly at a detector). Epi systems are especially suitable for photoluminescence assays, trans systems are especially suitable for absorbance assays, and oblique systems (with the incidence angle set above the critical angel) are especially suitable for total internal reflection assays, among others.

II.C. Sample-Support Devices

The sample-support device (104) generally comprises any mechanism for supporting one or more samples at a sample site in an examination area. In typical embodiments, the sample-support device allows for the receipt and/or transmission of light relative to one or more samples supported by the device. General examples of suitable sample-support devices can include trays, wells, tubes, containers, channels, chambers, frames, carriages, holders, slides, shelves, stages, housings, and/or the like. Specific examples of suitable sample-support devices can include microplates, PCR plates, microtiter plates, cell culture plates, biochips, hybridization chambers, chromatography plates, and/or microscope slides, among others. Specific locations in the sample-support device, such as wells in microplates, PCR plates, microtiter plates, and cell culture plates and array sites on biochips, can comprise assay sites. For example, microplates (and/or PCR plates, microtiter plates, and/or cell culture plates) can include arrays of 6, 12, 24, 48, 96, 384, 864, 1536, 3456, and/or 9600 such assay sites, among others. The sample-support devices can be configured to allow top detection (e.g., by having an open or at least partially transparent top), bottom detection (e.g., by having an at least partially transparent bottom), and/or side detection (e.g., by having an at least partially transparent side), among others. In some embodiments, the sample-support device can be configured, additionally and/or alternatively, to support an optical reference standard, for use before, during, and/or after sample analysis.

II.D. Registration Devices

The registration device generally comprises any mechanism for bringing a sample(s) and an examination area into registration, for analysis of the sample(s).

The registration device can move the sample (or associated sample-support device), the examination area, and/or both. For example, to effect relative movement of a sample and examination area, the registration device can include a driver, such as a stepper motor, that moves a carriage, tray, conveyor, stage, frame, and/or other structure or structures adapted to support the sample, an associated sample-support device, and/or a detector, among others. The registration device can move the sample and/or examination area in any suitable form or combination of motion(s), including, among others, (1) continuous or intermittent, (2) unidirectional, bidirectional, or multi-directional, and/or (3) rectilinear or curvilinear. Such movement can occur in the x, y, and/or z directions, and can occur parallel, perpendicular, and/or skewed to the excitation and/or emission axes.

The registration device can be under manual and/or automated control. Automated control can be particularly useful for analysis of plural samples, allowing successive registration of multiple samples and the examination site. Such control can be effected using any suitable mechanism, for example, moving a sample-support device and/or examination area in preselected increments and/or until preselected criteria are fulfilled. Such preselected increments can correspond to predefined separations between samples, or sample sites, as found in a microplate, PCR plate, biochip array, and/or the like. Such preselected criteria also can correspond to indicia (such as increased intensity) indicative of the presence of a sample, as found in bands on a separatory gel or column, among others. Such preselected criteria also can correspond to the positions of reference markings on an optical reference standard (e.g., portions 314 in FIG. 3 and/or portions 406 and 410 in FIG. 4, among others).

II.E. Color Separators

The color separator generally comprises any mechanism for spatially separating, or distributing, light according to its wavelength composition (or spectrum).

The color separator can use any suitable mechanism(s) and/or component(s) for separating light. Exemplary mechanisms can include diffraction, interference, and/or refraction, among others. Exemplary components can include (diffraction) gratings, interferometers, and/or prisms, among others. In some embodiments, the color separator can include two or more sequentially acting components, employing the same or different mechanisms, with the first component achieving a coarse color separation, and the second component achieving a finer or final color separation.

The color separator can separate multi-wavelength light by directing light with different wavelengths along different paths (e.g., in different directions, at different angles, etc.) The separation can be partial or complete, and can create bands or beamlets of light, which can be continuous or discrete, and which can be partially overlapping or completely distinct. The character of the separation typically will be determined at least in part by the character of the light being separated. Thus, input light with several well-spaced wavelength components can give rise to separated output light at several discrete (well-spaced) positions, while input light with closely or continuously spaced wavelength components can give rise to separated output light over a continuous set of positions.

The separated light generally can form any distinguishable pattern. Thus, the separated light can form a linear array, in which the wavelength of light varies with position along the line. Alternatively, the separated light can form a circular array, in which the wavelength of the light varies with distance from the center of the circle. In some embodiments, the color separator can produce light that is spectrally separated along a first axis, and spatially differentiated along a second axis at least substantially transverse to the first axis. In these embodiments, position along the first axis provides information about the spectral composition of light emitted from the sample, and position along the second axis provides information about the position from which the spectrally separated light arose in the sample.

The separated light can be directed onto a common detector, onto separate detectors, or onto a combination of detectors. The relationship between wavelength and position on the detector(s) can be determined empirically, for example, using input or calibration light of known wavelength(s). Alternatively, or in addition, the relationship between wavelength and position on the detector(s) can be determined theoretically, for example, by calculating the optical paths for light of different wavelengths. The position(s) of light on the detector can be determined by a variety of factors, including (1) the mechanism used to separate the light, (2) the angle(s) at which the light leaves the color separator, the distance between the color separator and the detector(s) (generally, greater distances between the color separator and detector(s) will give rise to greater separations between light of different wavelengths on the detector(s)), and/or (3) the type of pattern (e.g., linear versus circular) formed by the separated light, among others.

The spatial distribution or pattern of detected light can be converted into information about the distribution and identity(ies) of components of the sample, using any suitable method. These methods can include simply looking up a result in a look-up table (e.g., position (x,y) on the detector corresponds to light of wavelength $\lambda$ (or wavelengths within some extended range (e.g., $\lambda_1$ to $\lambda_2$)) emitted from position (X,Y) (or positions within some extended range) in the sample, evaluating a function expressing the relationship between these parameters, and/or the like. The desired result can be obtainable simply by noting qualitatively the presence or absence of light at a particular position on the detector (subject, in some cases, to some threshold amount), or it can be obtainable by determining quantitatively the amount of light (intensity, number of photons, amount of energy, etc.) detected at the position, among others.

The color separator can be disposed, in some embodiments, so that it acts only on light directed from a sample toward a detector, without acting on (or, in most cases, even contacting) light directed from a light source toward a sample.

The color separator can be included, in some embodiments, as part of a spectroscope or other instrument for producing and observing spectra from light or other electromagnetic radiation emitted from a sample.

Exemplary color separators are described further in U.S. Provisional Patent Application Ser. No. 60/584,525, filed Jun. 30, 2004, titled Distributed Light Detector of inventors Charles S. Vann and Steven Boege, which is incorporated herein by reference.

II.F. Detectors

The detector (106) generally comprises any mechanism for detecting light transmitted or otherwise originating from a sample and optionally converting the detected light into a representative signal.

Exemplary detectors can include film, charge-coupled devices (CCDs), intensified charge-coupled devices (ICCDs), charge injection device (CID) arrays, videcon tubes, photomultiplier tubes (PMTs), photomultiplier tube (PMT) arrays, position sensitive photomultiplier tubes, photodiodes, and/or avalanche photodiodes, among others. Such detectors can be capable of use in one or more detection modes, including (1) imaging and point-reading modes, (2) discrete (e.g., photon-counting) and analog (e.g., current-integration) modes, and/or (3) steady-state and time-resolved modes, among others. Particularly if used with a color separator, the detectors can be configured to receive a two-dimensional array of light, which may be separated along a first dimension according to position in a sample or sample array, and along a second dimension according to spectral composition. Toward this end, the detector can include bins for detecting light of different colors, for example, corresponding to light from different luminophores. These bins can be the same or different sizes, and can be formed of one or more sub-bins, or pixels, depending in part on the average separation between spectral peaks output by the color separator.

The detector can be used alone or in combination with various optics and/or other mechanisms (such as the optical relay structure described above). These optics and/or other mechanisms can be used to alter properties of the light (e.g., color, intensity, polarization, coherence, and/or size, shape, and/or numerosity of the light beam(s), as described elsewhere herein), prior to its detection. In some embodiments, the detector can be part of or coupled to a spectrograph or spectroscope for analyzing the spectral composition of the detected light.

II.G. Miscellaneous Optical Elements

The light-detection system, and/or components thereof, also can include miscellaneous optical elements capable of performing additional and/or duplicative optical functions. These optical elements can include (1) intensity filters (such as neutral density filters) for reducing the intensity of light, (2) spectral filters (such as interference filters, diffraction gratings, and/or prisms) for altering or selecting the wavelength(s) of light (e.g., for separating longer-wavelength emission light from shorter-wavelength excitation light, in single-photon photoluminescence, and/or for separating shorter-wavelength emission light from longer-wavelength excitation light, in multi-photon photoluminescence), (3) polarization filters (such as "polarizers") for altering or selecting the polarization of light, (4) "confocal optics elements" (such as an aperture or slit positioned in an intermediate image plane) for reducing or eliminating out-of-focus light, (5) beam collimators for converting input light (particularly diverging input light) into an at least substantially collimated light beam, (6) beam expanders for increasing the cross-sectional area of a beam of light, (7) beam homogenizers (such as a fiber optic cable or liquid light guide) for enhancing the spatial uniformity of light, and/or (8) reference monitors for correcting for variations (e.g., fluctuations and/or inhomogeneities) in light produced by a light source and/or other optical elements. These elements can be functional in one or more of the space, time, and/or frequency domains, as necessary or desired.

The relative positions of any intensity, spectral, polarization, and/or other optical elements generally can be varied without affecting the operation of the light-detection system. In addition, if there is more than one optical path, for example, to permit top and bottom or oblique illumination and/or detection, optical elements can be shared and/or used independently in each path. The particular order, positions, and combinations of optical elements for a particular experiment can depend on the apparatus, the assay mode, and the sample (target material), among other factors. In some cases, optical elements can be associated with an exchange mechanism, such as a wheel or slider, that allows convenient and automatable placement and exchange of optical elements by rotating, sliding, or otherwise bringing preselected optical elements into or out of the optical path.

II.H. Controllers

The controller generally comprises any mechanism for controlling components and/or other aspects (including calibration and/or monitoring) of the light-detection system. These components and/or other aspects can include the light source, optical relay structures, registration device, detector, and/or optical reference standard, among others. For example, the controller can determine and/or change (1) the wavelength, intensity, and/or (spatial and/or temporal) uniformity of light produced by the light source, (2) the order and timing of sample delivery by the registration device and image acquisition by the detector, and/or (3) the wavelength and/or intensity of light detected by the detector, among others. The controller can include hardware, software, firmware, and/or a combination thereof, and can be any device, or combination of devices, adapted to store and execute instructions to control associated detection system components. The controller can include one or more of various devices, such as a computer, computer server, microprocessor, memory, logic unit, and/or processor-based system capable of performing a sequence of logic operations. In addition, processing can be centralized (with two or more components sharing a common controller) and/or distributed (with one or more components having their own dedicated controllers, acting alone, or connected to one another and/or a central controller).

III. APPLICATIONS

Light-detection systems calibrated and/or monitored using optical reference standards in accordance with the present teachings can be used for any suitable purposes, such as detecting and/or monitoring the occurrence of, and/or changes in, light or other forms of radiation received from one or more suitable samples.

The detection or monitoring of light can be performed qualitatively and/or quantitatively. Qualitative detection can include measurement of the presence or absence of a signal, and/or a change in a signal from present to absent, or absent to present, among others. Here, presence or absence can be in reference to a whole signal (such as any light) and/or a component of the signal (such as light of a particular wavelength, polarization, and/or the like). The signal, and/or components thereof, can arise from the sample itself and/or from labels (or other reporters) attached to or otherwise associated with the sample. Quantitative detection can include measurement of the magnitude of a signal, such as an intensity, wavelength, polarization, and/or lifetime, among others. The quantified signal can be used alone and/or compared or combined with other quantified signals and/or calibration standards. The standard can take the form of a calibration curve, a calculation of an expected response, and/or a control sample measured before, during, and/or after measurement of the sample of interest.

The detected or monitored light can be used for any suitable purpose, for example, to determine the presence, absence, amount, concentration, activity, and/or physical properties (including interactions) of an analyte (such as a photoactive analyte) in a sample. Here, the analyte can be the actual moiety of interest and/or a reporter moiety (such as a luminophore) that reports on the actual moiety of interest.

The moiety of interest can be a reaction component. Exemplary reaction components can include an enzyme, enzyme substrate, enzyme product, and/or enzyme modulator (e.g., agonist and/or antagonist). Suitable reactions can occur in vivo and/or in vitro, for example, as part of a cell-lysis experiment and/or a polymerase chain reaction (PCR) preparation. Exemplary reaction components also can include precursors and/or products of a synthetic pathway, such as an amino acid, peptide, protein, nucleotide, oligonucleotide, nucleic acid polymer, carbohydrate, fatty acid, lipid, and/or the like.

The moiety of interest also can be the subject and/or product of a separatory process, such as on a chromatograph, gel, column, and/or the like. Here, the separatory process can include single processes, such as columns giving rise to fractions, and/or multiple processes, such as parallel lanes on a gel giving rise to sets of bands.

The moiety of interest also can be the subject of a sequencing process, such as a peptide, protein, oligonucleotide, and/or nucleic acid (RNA or DNA) sequencing process. Here, the sequence can include amino acid sequence, nucleotide or base sequence (e.g., G, C, T, A, U, etc.), and so on, and the sequencing process can include generating fragments (or other derivatives) of the moiety to be sequenced and labeling those fragments (before or after their generation) with different luminophores. Thus, in nucleic acid sequencing, the presence of a G, C, T, A, or U at a particular position in a moiety of interest, or in a fragment or derivative thereof, can be determined by the identity of an associated luminophore.

The moiety of interest also can be the subject of an identification, or affinity, process, such as a northern, western, and/or southern blot.

In some cases, the effect of some condition on the moiety of interest can be determined, for example, by comparing results in the presence of the condition with predicted and/or measured results in the absence of the condition and/or the presence of another condition. Exemplary conditions can include presence or absence of a modulator (agonist or antagonist) or cofactor, and/or changes in temperature, concentration, pH, osmolarity, ionic strength, and/or the like.

The sample can include any appropriate material, with any suitable origin. For example, the sample can include and/or be derived from a biomolecule, organelle, virus, cell, tissue, organ, and/or organism. The sample can be biological in origin and/or synthetically prepared. A sample optionally can be, or can be derived from, a biological sample, such as a sample prepared from a blood sample, urine sample, fecal sample, saliva sample, and/or mucous sample, obtained using any suitable physiological sampling method, such as a swipe or a smear, among others. A sample optionally can be, or can be derived from, an environmental sample, such as an air sample, a water sample, or a soil sample. A sample can be aqueous, and yet can contain biologically compatible organic solvents, buffering agents, inorganic salts, or other components known in the art for assay solutions. Suitable samples (or compositions) can include compounds, mixtures, surfaces, solutions, emulsions, suspensions, cell cultures, fermentation cultures, cells, suspended cells, adherent cells, tissues, secretions, and/or derivatives and/or extracts thereof. Depending on the assay, the term "sample" can refer to the contents of a single sample site (e.g., microplate well) or of two or more sample sites.

IV. EXAMPLES

The following examples describe selected aspects of the present teachings. These selected aspects include, among others, exemplary apparatus, methods, and compositions for detecting light. The selected aspects can be combined with other aspects in the same and/or other examples, and/or in other portions of these teachings, as suitable and/or desired. These examples are included for illustration and are not intended to limit or define the entire scope of the disclosed concepts.

Example 1

Exemplary Subtraction-Based Reference Standards

This example describes an exemplary subtraction-based reference standard 500, in accordance with aspects of the present teachings; see FIGS. 5-9. The exemplary standard can be used with multi-luminophore photoluminescence systems, among others, including but not limited to carboxyfluorescein (FAM) and carboxy-X-rhodamine (ROX) (or similar green and red emitting) dual-luminophore systems.

FIG. 5 is a schematic sectional view of reference standard 500. This exemplary standard, which was described above in more detail in Section I.D, can include several components: (1) a support element 502, (2) a broadband photoluminescent element 504, (3) at least one subtractive or spectral filter element 506a,b,c, (4) an intensity filter element 508, (5) a coating element 510, and/or (6) a light-blocking element (or mask) 512, among others. Here, these components are arranged as a series of at least substantially planar layers, in the indicated order; however, more generally, these components can have any suitable form, and any suitable order. Moreover, here, the broadband photoluminescent component includes Ultem® 1000 polyetherimide (PEI) plastic polymer, and the spectral filter components include cold-coating filter materials configured to transmit light with FAM and ROX spectra. Overall, the reference standard can take any suitable form, for example, a 3.10-inch width×6.60-inch length×1/16-inch height sheet, corresponding to the approximate size of a Society for Biomolecular Screening (SBS) standard microplate used in common fluorescence detection systems, among others.

Figure 6:
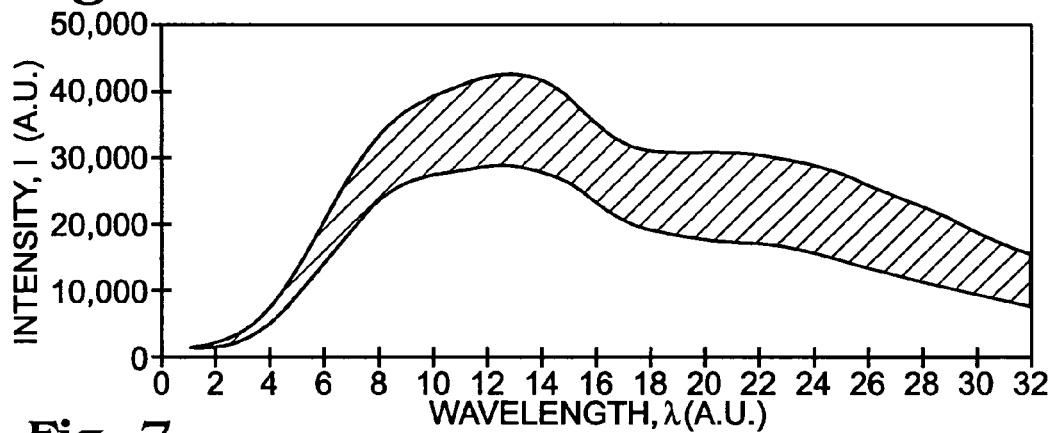
FIG. 6 is an exemplary emission spectrum for Ultem® 1000 plastic, showing relative emission intensity as a function of emission wavelength, following excitation at a fixed excitation wavelength, in accordance with aspects of the present teachings. The shaded envelope is constructed from the lowest and highest intensities measured at each emission wavelength, based on analysis of 384 identically prepared samples.

FIG. 6 is a plot of an exemplary emission spectrum for broadband photoluminescent component 504, from reference standard 500. The emission spectrum is a plot of the relative intensity of photoluminescence emitted from the photoluminescent component as a function of the wavelength of the photoluminescence, following excitation with suitable excitation light (i.e., excitation light having a wavelength (or range of wavelengths) capable of inducing photoluminescence emission from the photoluminescent component). The spectrum represents photoluminescence emitted by uncoated Ultem® 1000 plastic, following excitation at 488 nm (e.g., using an argon ion laser). Ultem® 1000 plastic can be translucent, rather than optically clear, with a yellow tint and a broad photoluminescence emission spectrum. In addition, Ultem® 1000 plastic can have one or more advantageous mechanical properties, such as durability and/or high-melting temperature, among others. The spectrum shows an envelope of values constructed by displaying the highest and lowest values at each wavelength, based on measurements of 384 similarly prepared samples.

Figure 7:
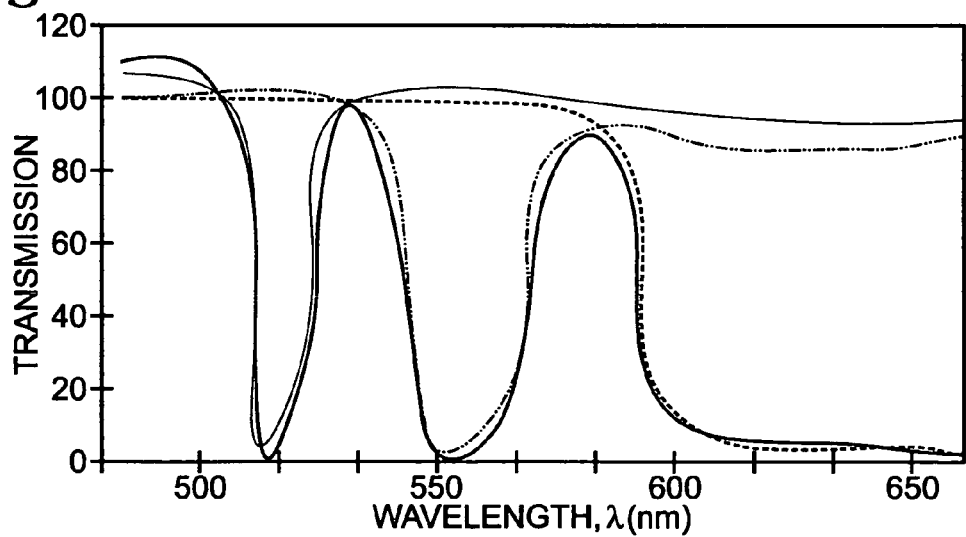
FIG. 7 is a plot of transmission versus wavelength showing individual and composite transmission spectra of subtractive elements of the subtraction-based, Ultem®-1000-plastic-containing reference standard of FIG. 6. The dashed, dot-dashed, and thin solid lines represent transmission spectra of individual layers. The thick solid line represents the composite transmission spectrum.

FIG. 7 is a plot of individual and composite transmission spectra for filter elements 506a,b,c, from reference standard 500. The transmission spectra are plots of relative transmissivity as a function of wavelength. In these spectra, higher values of the transmissivity correspond to relatively greater transmission (and lesser absorption) of light, and lower values of the transmissivity correspond to relatively lesser transmission (and greater absorption) of light. Here, there are three filter layers, each with its own transmission spectrum: (1) layer 1 (dashed line), a short-pass filter, that generally transmits short-wavelength light, and generally blocks long-wavelength light, (2) layer 2 (thin solid line), a first band-reject (or notch) filter, that generally rejects light at a first intermediate wavelength, while generally passing light with relatively shorter and longer wavelengths, and (3) layer 3 (dot-dashed line), a second band-reject (or notch) filter, that generally rejects light at a second intermediate wavelength, while generally passing light with relatively shorter and longer wavelengths. The combined or composite action of these three filter layers (thick solid line) creates a bandpass filter that generally transmits light at two distinct wavelengths (or ranges of wavelengths) and that generally blocks light with other (nearby) wavelengths. For example, in a FAM/ROX dual-luminophore system, the optical coating typically will have a relatively narrow bandpass transmission peak near the emission band of each luminophore, that is, near about 520-nm (green) wavelength for the FAM dyes, and near about 600-nm (red) wavelength for the ROX dye, among others. Moreover, if excitation and emission occur on the same side of the reference standard, as in epi-fluorescence mode, the combined or composition action of the three filter layers also can pass light at wavelengths shorter or longer than those of the two transmission peaks, for single-photon or multi-photon excitation, respectively. For example, for single-photon excitation of FAM and ROX dyes, the optical coating typically will pass light near about 488-nm (blue-green) wavelength. Suitable filter layers are available commercially. For example, suitable cold coatings can be obtained from Chroma Technology Corp. (Rockingham, Vt.) for application to the support and/or broadband component.

Figure 8:
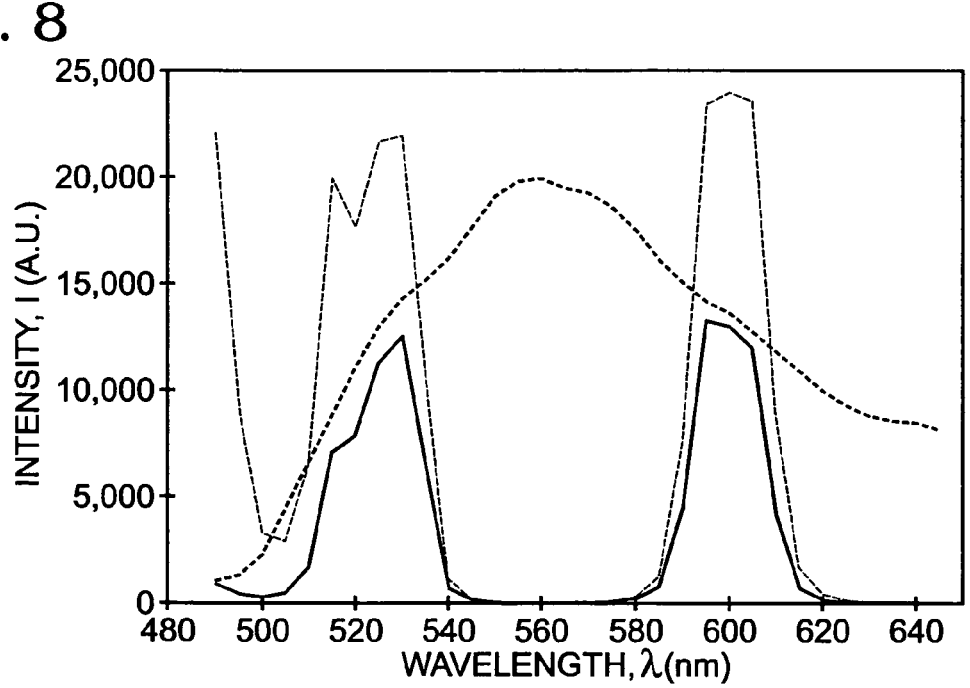
FIG. 8 is a plot of an exemplary calculated emission spectrum for the subtraction-based, Ultem®-1000-plastic-containing reference standard of FIG. 6. The calculated emission spectrum (solid line) is a product of the emission spectrum of a broadband photoluminescent component (thick dashed line) and the composite transmissivity of various spectral filter components (thin dashed line).

FIG. 8 is a plot of an exemplary calculated emission spectrum for reference standard 500. The calculated emission spectrum (solid line) is a product of the emission spectrum of broadband photoluminescent component 504 (thick dashed line; see also FIG. 6) and the composite transmissivity of filter components 506a-c (thin dashed line; see also FIG. 7).

Figure 9:
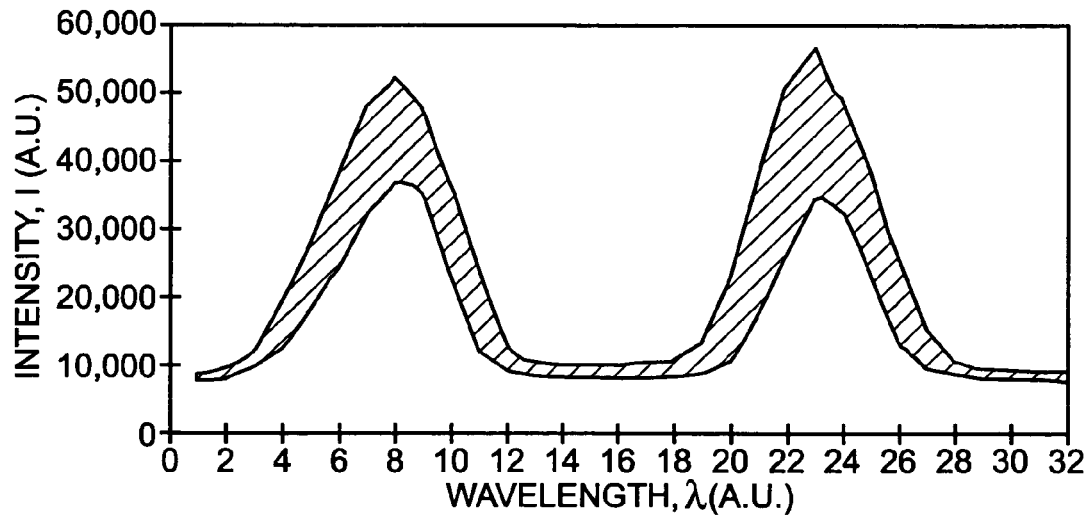
FIG. 9 is an exemplary emission spectrum for a subtraction-based, Ultem®-1000-plastic-containing reference standard, showing relative emission intensity as a function of emission wavelength, following excitation at a fixed excitation wavelength, in accordance with aspects of the present teachings. The shaded envelope is constructed from the lowest and highest intensities measured at each emission wavelength, based on analysis of 384 identically prepared samples.

FIG. 9 is a plot of an exemplary measured emission spectrum for reference standard 500. The spectrum, measured on an Applied Biosystems (AB) Sequence Detection System 7900 instrument, includes two distinct, relatively narrow peaks, as predicted in FIG. 8. In this embodiment, the intensities of these peaks are about one-sixth those of the broadband component alone; however, in other embodiments, the intensities can be increased using other substrate materials and/or filter components. This spectrum, like that in FIG. 7, shows an envelope of values defined by the highest and lowest values at each wavelength, based on measurements of 384 wells.

Example 2

Exemplary Addition-Based Reference Standards

Figure 10:
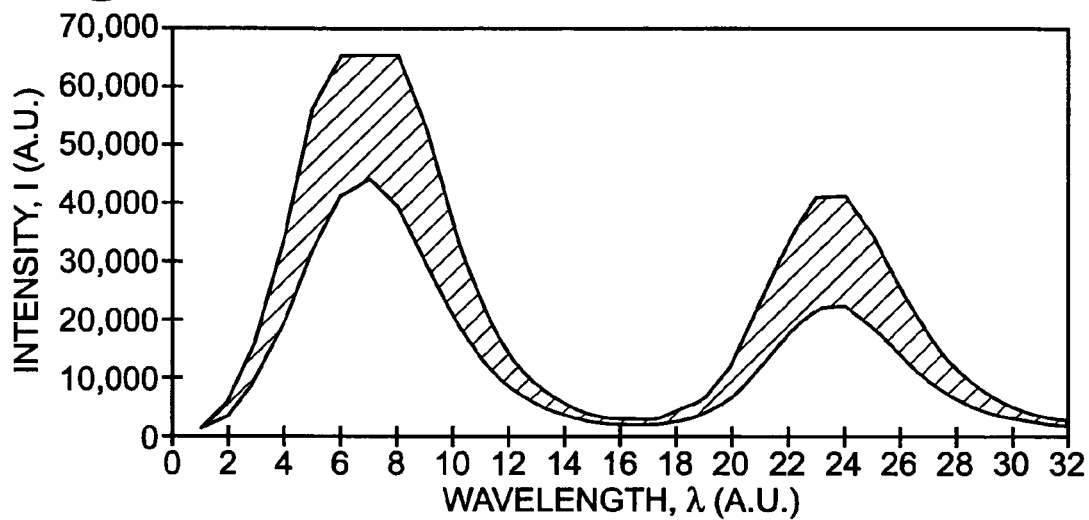
FIG. 10 is an exemplary emission spectrum for an addition-based, photoluminescent-nanocrystal-containing reference standard, showing relative emission intensity as a function of emission wavelength, following excitation at a fixed excitation wavelength, in accordance with aspects of the present teachings. The shaded envelope is constructed from the lowest and highest intensities measured at each emission wavelength, based on analysis of 20 identically prepared samples.
Figure 11:
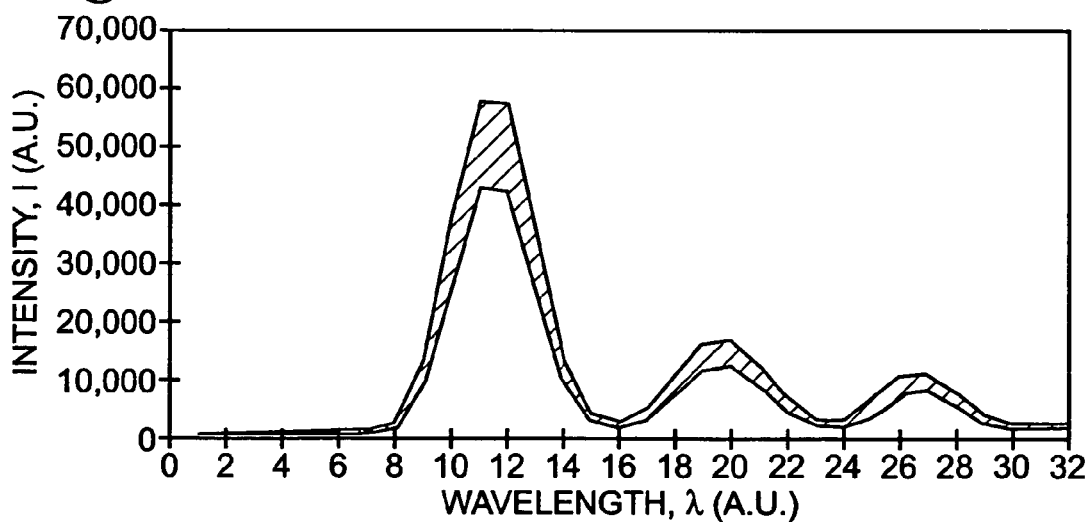
FIG. 11 is an exemplary emission spectrum for an addition-based, luminescent-glass-containing reference standard, showing relative intensity as a function of emission wavelength, following excitation at a fixed excitation wavelength, in accordance with aspects of the present teachings. The shaded envelope is constructed from the lowest and highest intensities measured at each emission wavelength, based on analysis of a plurality of identically prepared samples.

This example describes exemplary addition-based reference standards, in accordance with aspects of the present teachings; see FIGS. 10 and 11. The exemplary standards can be used with multi-luminophore photoluminescence systems, among others, including but not limited to carboxyfluorescein (FAM) and carboxy-X-rhodamine (ROX) (or similar green and red emitting) dual-luminophore systems. These standards generally can include any combination of two or more luminophores, with different emission spectra, and optionally with similar or overlapping excitation spectra (such that the combinations of luminophores can be excited using light of similar wavelength). The exemplary standards can include (A) photoluminescent nanocrystals ("quantum dots") and/or (B) photoluminescent glass, among others, as described below.

A. Photoluminescent Nanocrystal-Based Reference Standards

This section describes exemplary photoluminescent nanocrystal-based reference standards; see FIG. 10. Photoluminescent nanocrystals, as used herein, generally can include any small, solid-state photoluminescent compositions, including but not limited to "quantum dots."

Photoluminescent nanocrystals can include (1) a core, (2) a shell, and (3) an optional coating, among others. The core typically is the primary source of the nanocrystal's photoluminescence, with the composition and size of the core (primarily) determining the properties of this photoluminescence. The composition of the core can coarsely determine emission properties. For example, cadmium sulfide (CdS) cores can be particularly suitable for ultraviolet-blue emission, cadmium selenide (CdSe) can be particularly suitable for visible emission, and cadmium telluride (CdTe) can be particularly suitable for far-red and near-infrared emission, among others. The size of the cores can more finely determine emission properties. For example, relatively large (>6-nm diameter) CdSe cores can be used to prepare 655-nm emitting nanocrystals, and relatively small (<3-nm diameter) CdSe cores can be used to prepare 525-nm emitting nanocrystals. The cores generally can have any suitable shape, including spheres, rods, and/or pyramids, among others. The shell typically surrounds the core, functioning to strengthen and stabilize photoluminescence emission. The shell can be formed of any suitable material(s). The coating typically surrounds the shell (and thus the core), functioning to determine the hydrophilicity and/or reactivity of the nanocrystal, among others. The coating can be formed of any suitable material(s), including hydrophobic and/or hydrophilic materials, reactive groups, binding groups (e.g., antibodies or antigens. avidin or biotin, lectins or sugars, etc.), and so on.

Photoluminescent nanocrystal-based optical reference standards (like other optical reference standards in accordance with the present teachings) can take any suitable format, including, among others, (1) discrete formats, in which the luminophores are disposed at discrete sites (e.g., corresponding to microplate wells), and/or (2) continuous formats, in which the luminophores are disposed continuously (e.g., in and/or on a microscope slide), as described below.

A.1. Discrete Embodiments

Discrete formats correspond to reference standards in which the luminophores are disposed at discrete sites in and/or on the reference standard. Exemplary discrete formats can include microplate-based embodiments, among others, including wet and dry embodiments. In wet embodiments, soluble or suspendable luminophores such as photoluminescent nanocrystals can be dissolved or suspended in an appropriate (e.g., aqueous) solution, before or after being dispensed into wells of a microplate. Suitable microplates can have 96, 384, and/or 1536 wells, among others. Wet microplate-based standards could provide various benefits. For example, wet standards could position the luminophores in the reference standard in the same or similar environment (solution and/or sample holder) as the luminophore(s) in the sample, to account for any contribution to the signal from the sample holder. Moreover, wet standards could position the luminophores in the standard at the designed focal point of the optical detection system used in the assay.

Discrete (microplate and/or other well or fluid based) embodiments can be covered or sealed, using any suitable mechanism and material, to increase their robustness and durability. Suitable seal mechanisms can include pressure-sensitive adhesive (PSA), heat seal material (where one or more layers melts, flows, and bonds to the microplate (or other sample holder)), ultrasonic welding, and/or similar devices and processes. Exemplary embodiments can include a silicone-based adhesive on a clear polyolefin laminate backing (polypropylene/polyethylene terephthalate (PP/PET)) with a white polyester film release liner, and/or a heat-sealable polyester-based film laminate of PET/MR, in which the seal optionally can fuse with the microplate material. In some embodiments, with or without a cover or seal, an evaporation inhibitor such as DMSO can be added to the aqueous solution to further prevent evaporation. In these embodiments, if any air leaks do occur in the seal, the DMSO will act to absorb ambient moisture.

Luminophores can be suspended, in some embodiments, in a low-fluorescing gel, polymer, epoxy, and/or other solid or semi-solid material medium, before or after being dispensed into a well or other embodiment. The fluid compartment can again be sealed, transiently or permanently, by an acceptable sealing material. The suspension material and optional sealing would lower the risk of unwanted leaks and spills. Specific examples of alternative suspension media include polymer gels, agarose gels, acrylamide gels, optical grade epoxies, and/or others.

Luminophores can be "dried down," in some embodiments, after being dispensed—suspended or dissolved—into a fluid compartment, by evaporating off the carrier solvent(s). The dried-down luminophores, such as photoluminescent nanocrystals, still would exhibit their stable fluorescence spectra, but without the risk of liquid spills. This approach is particularly suitable as a standard for adherent cell assays, because it positions the luminophores in the standard at the same focal height as the cells in the assay. The microplates could be sealed, transiently or permanently, by an acceptable seal material, as above.

FIG. 10 is an exemplary emission spectrum for an addition-based, photoluminescent-nanocrystal-containing reference standard, showing relative emission intensity as a function of emission wavelength, following excitation at a fixed excitation wavelength. The shaded envelope is constructed from the lowest and highest intensities measured at each emission wavelength, based on analysis of 20 identically prepared samples. Here, exemplary photoluminescent nanocrystals with emission at 525 nm and 608 nm were mixed and suspended in aqueous solution, and pipetted into wells in a 384-well microplate, for measurement of the emission spectrum. Specifically, the 525-nm and 608-nm nanocrystals were suspended at concentrations of 0.55 µM and 0.034 µM, respectively, and then 10 µL of the resulting solution was added to each well measured. The molar concentration of the suspended nanocrystals optionally can be correlated or matched to the appropriate molar concentrations of dyes, such as FAM and ROX dyes, commonly used in biological assays. Suitable microplates (for any discrete embodiments) can include, among others, the AB 96-well microplate, the AB 384-well microplate, and the AB 384-well Micro Fluidic Card (MFC) (Applied Biosystems, Foster City, Calif.). Suitable light-detection systems (for any embodiments) can include, among others, the AB Sequence Detection Systems Models 7000, 7300, 7500, 7700, and 7900 (Applied Biosystems), among others.

In various embodiments, instruments for thermal cycling can include a heated lid with apertures corresponding to wells to be interrogated and a thermal block to provide thermal contact with the wells. The luminescence reference plate can contact to the block to establish the appropriate temperature for the light-producing elements. The luminescence reference plate includes an insulator on the upper side of the carrier with light-blocking elements to prevent contact with the heated lid that can avoid thermal short. The carrier can be configured as apertures on the top portion forming the light-blocking elements. The apertures in the carrier can be configured to align with the apertures in the heated lid. The carrier can be configured with recesses on the bottom portion where the recesses on the bottom portion correspond to the apertures on the top portion. The top portion and bottom portion of the carrier can be configured to bound a layer of media forming the light-producing elements. The recesses on the bottom portion of the carrier can include black paint to provide a background correction. A user of the luminescence reference plate can obtain the luminescent calibration from the top portion on the carrier and then flip the luminescence reference plate over to obtain a black background correction.

A.2. Continuous Embodiments

Continuous formats correspond to reference standards in which luminophores are disposed continuously throughout part or all of the reference standard. This "continuous" distribution can be uniform or variable, in one, two, or three dimensions.

Exemplary embodiments can include (1) a support element, such as a planar support element, and (2) a light-producing layer (or layers) of fluorescence reference standard material, such as photoluminescent nanocrystals. The light-producing layer(s) can be formed on an outer surface of the support element, and/or sandwiched between layers (or other portions) of the support element. The support element and/or light-producing layer(s) optionally can be covered with a coating, for example, as described above.

The light-producing layer(s) can be produced by any suitable mechanism, such as a solid layer than can be transferred intact to the support structure (like a cellophane), or as a liquid or vapor applied to or contacted to the support element. For example, in the latter case, to produce a thin sheet of fluorescence reference standard material with a continuous and uniform fluorescent surface, the luminophores can be suspended in an appropriate solution and spin coated onto the support element. For a glass substrate, appropriately charged luminophores can be spin coated and adhered onto the glass surface. For a more durable solution having a plastic substrate, luminophores that are soluble, or suspended, in organic solvents can be used. The appropriately coated luminophores can be suspended in organic solvents and put into a fluorinated polymer. In this case, the organic solvents can be dried off, leaving the luminophores in the plastic polymer.

B. Photoluminescent-Glass-Based Reference Standards

This example describes exemplary photoluminescent glass reference standards; see FIG. 11. Glasses, as used herein, generally can include any super-cooled liquids or noncrystalline solids, with intrinsic luminescence and/or with "added" luminophores. The glass can be used as a continuous slab, alone or in conjunction with a mask that limits excitation and/or emission to discrete locations. Alternatively, or in addition, the glass can be disposed at discrete locations, for example, in microplate wells. Glasses can have a number of potential advantages, including sensitivity (efficiency), durability (e.g., to temperatures above 100° C.), wide excitation band, large Stokes' shift, and so on. The number of bands and the relative intensities of the bands can be adjusted by using suitable filter materials (just like with the subtraction-based standards).

FIG. 11 shows an exemplary emission spectrum obtained with Lumilass G9™ glass, a commercially available photoluminescent glass (SUMITA Optical Glass, Inc.). Suitable photoluminescent glasses can include (1) Lumilass R7™ glass, which can be excited with ultraviolet light in the 200-420 nm range, and which emits red fluorescence at about 610 nm, among others, (2) Lumilass G9 glass, which can be excited with ultraviolet light in the range 200-390 nm, and which emits green florescence at about 540 nm, among others, and (3) Lumilass B™ glass, which can be excited with ultraviolet light in the range 200-400 nm, and which emits blue fluorescence at about 405-410 nm, among others.

Example 3

Exemplary Light-Detection System

Figure 12:
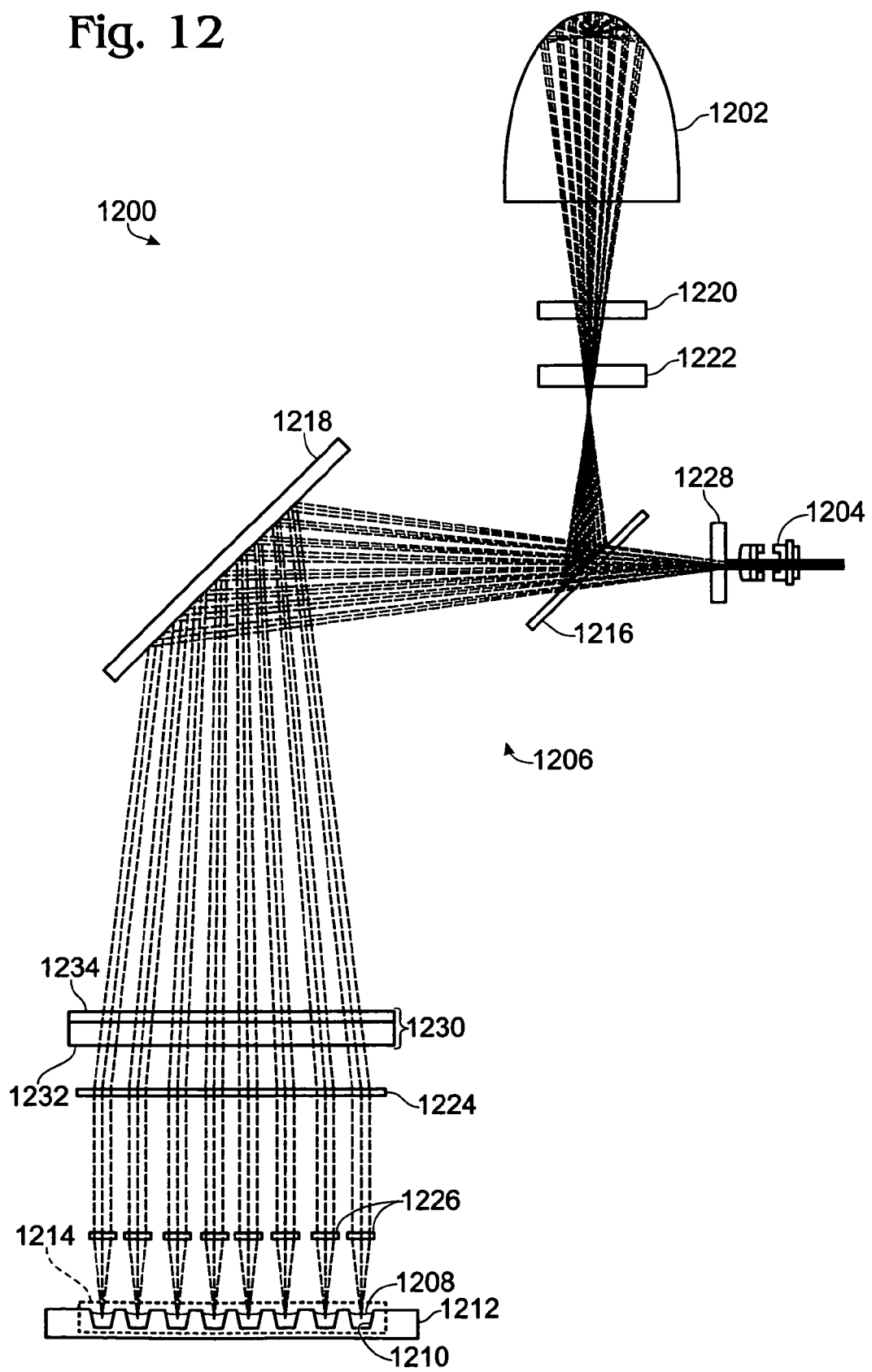
FIG. 12 is a schematic sectional view of another exemplary light-detection system, showing selected optical components and an optical reference standard, in accordance with aspects of the present teachings.

This example describes an exemplary light-detection system 1200, including an associated optical reference standard, in accordance with aspects of the present teachings; see FIG. 12. This exemplary embodiment is described with reference to specific components; however, these components can be omitted or substituted with other components, as appropriate or feasible.

Light-detection system 1200 includes (1) a light source 1202 (e.g., a vertically oriented tungsten halogen lamp), (2) a detector 1204 (e.g., a charge-coupled device (CCD) camera), and (3) an optical relay structure 1206 for directing light from the light source onto one or more samples 1208 disposed in wells 1210 of a multiwell sample holder 1212 such as a microplate at an examination site 1214, and from the sample(s) to the detector. The optical relay structure, in the pictured embodiment, includes a (long-pass) dichroic beamsplitter 1216 for separating and properly routing excitation and emission light, and a fold mirror 1218 for turning excitation and emission light toward and away from the samples, respectively. The light-detection system further may include an infrared-blocking "hot mirror" 1220 for filtering out infrared light, an excitation filter 1222 for filtering out additional unwanted (e.g., selected visible) excitation light, a Fresnel lens 1224 and well lenses 1226 for directing light onto the samples, and an emission filter 1228 for filtering out stray excitation light mixed with the emission light.

The light-detection system optionally includes and/or can be used with an optical reference standard 1230. This reference standard is positioned, in the pictured embodiment, in the optical path between the fold mirror (1218) and the Fresnel lens (1224). The reference standard, which resembles reference standard 300 (embodiment "a") in FIG. 3, includes a light-producing component 1232 and a light-blocking or mask component 1234. The reference standard functions like a multi-well version of optical reference standard 110 in FIG. 1.

Example 4

Miscellaneous Matters

This example describes miscellaneous aspects of light-detection systems and optical reference standards, in accordance with aspects of the present teachings.

The optical reference standard can be used for any suitable purpose, consistent with these and/or other applications. These purposes optionally can include, among others, (1) focusing images of microplate wells onto a CCD camera by adjusting a focusing lens for maximum fluorescence intensity from the reference standard, (2) rotating a CCD camera so that pixel columns are parallel to the rows or columns of the microplate by aligning the fluorescence spectra from the reference standard, (3) calibrating the optics to a known spectral wavelength (or wavelengths), (4) adjusting the multiple components of a light detection system, such as lasers, beam splitters, neutral density filters, and/or the like, (4) verifying instrument performance (alignment and event size and count) with specific sizes, and with specific numbers, of exemplary fluorescent targets (particularly for cell counting devices), (5) locating grids within a microfluidic array device, and/or (6) correlating instrument response with the concentration of organic dye. Elaboration on these purposes, and/or additional purposes, are described elsewhere herein.

The optical reference standard may have any properties suitable with its function. These properties optionally can include, among others, (1) an ability to withstand temperatures normally achieved in fluorescence detection systems, such as real-time polymerase chain reaction (PCR) systems, such that it does not melt at temperatures below about 110° C., (2) few and/or minor lot-to-lot variations in optical and physical properties, (3) high-intensity narrow-emission peaks (e.g., full width at half-max $\leq 15$ nm) at the wavelengths detected by the instrumentation, (4) uniform fluorescence emission spectra across all discrete wells, or positions, or that are continuously uniform across the entire homogenous surface, (5) stability for long periods of time (e.g., >5 years), with little or no degradation from photobleaching, and/or (6) low cost. The emission peaks can be centered, in some embodiments, at about 520 nm corresponding to FAM dye and at about 600 nm corresponding to ROX dye, when excited by a 488-nm wavelength light source, and/or in other embodiments at the fluorescence wavelengths of Cy5 and Cy5.5 dyes, when excited by a red laser, and/or so on.

Instrument performance for cell-counting instruments can be validated using patterns of luminescent targets. Toward this end, a mask containing the desired shape, size, and quantity of fluorescence targets can be applied over the fluorescence reference standard. Each target is merely a hole through the mask material, which is opaque and non-fluorescing, thereby providing a clear aperture of the desired shape and size to the fluorescence reference standard material underneath. The mask can be an etched or machined chip. The mask can include several wells that mimic the wells of normally used microplates (or other sample holders), for example, a 1536-well SBS standard microplate. A particular pattern of targets can be contained within each well of the mask. The particular pattern in a well will depend on its function, that is, whether the standard is used for alignment, and/or to verify event size and count.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein.

What is claimed:

1. A luminescence reference plate for biological samples, the reference plate comprising:
   a support, wherein the support is configured to provide structural support for the luminescence reference plate;
   light-producing elements, wherein the light producing elements comprise a layer positioned on the support;
   light-blocking elements bounding the light-producing elements, wherein the light-blocking elements comprise a mask;
   at least one of a spectral filter layer, an intensity filter layer, and a protective coating layer positioned between the light producing elements and the mask; and
   an insulator coupled to the light-blocking elements, wherein the reference plate with an insulator is adapted for use in a thermal cycler having a heated lid.

2. The luminescence reference plate of claim 1, wherein the light-producing elements comprise a subtraction-based material.

3. The luminescence reference plate of claim 2, wherein the subtraction-based material comprises Ultem.

4. The luminescence reference plate of claim 1, wherein the light-producing elements comprise an addition-based material.

5. The luminescence reference plate of claim 4, wherein the addition-based material comprises photoluminescent-nanocrystal-containing material.

6. The luminescence reference plate of claim 5, wherein the material comprises quantum dots.

7. The luminescence reference plate of claim 4, wherein the addition-based material comprises a luminescent-glass-containing material.

8. The luminescence reference plate of claim 1, wherein the light-producing elements are formed from a multi-layer media between a top portion of a carrier and a bottom portion of the carrier.

9. The luminescence reference plate of claim 8, wherein the top portion of the carrier forms the light-blocking elements and couples to the insulator.

10. The luminescence reference plate of claim 9, the bottom portion of the carrier comprises a black background.

11. The luminescence reference plate of claim 10, wherein the black background comprises an array of recesses in the bottom portion of the carrier, wherein the recesses comprises black paint.

12. A system for calibrating an instrument for thermal cycling of a biological sample, the system comprising:
 a thermal cycling device comprising:
  a light source;
  an optical relay structure;
  a detector;
  a thermal block;
  a heated lid; and
 a luminescence reference plate in optical communication with the light source and detector through the optical relay structure, wherein the luminescence reference plate contacts with the heated lid and the thermal block, the luminescence reference plate comprising:
  light-producing elements, wherein the light producing elements comprise a layer positioned on the support;
  light-blocking elements bounding the light-producing elements, wherein the light-blocking elements comprise a mask;
  at least one of a spectral filter layer, an intensity filter layer, and a protective coating layer positioned between the light producing elements and the mask; and
  an insulator coupled to the light-blocking elements, wherein the reference plate with an insulator is adapted for use in the thermal cycler with the heated lid.

13. The system of claim 12, wherein the light-producing elements comprise at least one of a subtraction-based material and an addition-based material.

14. The system of claim 13, wherein the material comprises at least one of Ultem, photoluminescent-nanocrystal-containing material, quantum dots, luminescent-glass-containing material.

15. The system of claim 12, wherein the light-producing elements are formed from a multi-layer media between a top portion of a carrier and a bottom portion of the carrier.

16. The system of claim 15, wherein the top portion of the carrier forms the light-blocking elements and couples to the insulator.

17. The system of claim 16, the bottom portion of the carrier comprises a black background.

18. The system of claim 17, wherein the black background comprises an array of recesses in the bottom portion of the carrier, wherein the recesses comprises black paint.

* * * * *